United States Patent
Wu

(10) Patent No.: US 10,098,384 B2
(45) Date of Patent: Oct. 16, 2018

(54) ATOMIZED LIQUID STORAGE DEVICE AND ATOMIZER

(71) Applicant: SHENZHEN JIESHIBO TECHNOLOGY CO., LTD., Shenzhen, Guangdong (CN)

(72) Inventor: Jianyong Wu, Guangdong (CN)

(73) Assignee: SHENZHEN JIESHIBO TECHNOLOGY CO., LTD., Shenzhen (CN)

( * ) Notice: Subject to any disclaimer, the term of this patent is extended or adjusted under 35 U.S.C. 154(b) by 198 days.

(21) Appl. No.: 14/988,770

(22) Filed: Jan. 6, 2016

(65) Prior Publication Data
US 2017/0079328 A1    Mar. 23, 2017

(51) Int. Cl.
| | |
|---|---|
| F24F 6/08 | (2006.01) |
| A24F 47/00 | (2006.01) |
| B65D 39/00 | (2006.01) |
| A61M 15/06 | (2006.01) |
| A61M 11/04 | (2006.01) |

(52) U.S. Cl.
CPC ......... *A24F 47/008* (2013.01); *A61M 11/042* (2014.02); *A61M 15/06* (2013.01); *B65D 39/0005* (2013.01); *A61M 2205/276* (2013.01); *A61M 2205/3653* (2013.01); *A61M 2205/6027* (2013.01); *A61M 2205/6054* (2013.01)

(58) Field of Classification Search
None
See application file for complete search history.

(56) References Cited

U.S. PATENT DOCUMENTS

| | | | | |
|---|---|---|---|---|
| 2015/0342257 | A1* | 12/2015 | Chen | H05B 3/06 392/390 |
| 2015/0351454 | A1* | 12/2015 | Huang | F22B 1/284 392/394 |
| 2016/0143364 | A1* | 5/2016 | DePiano | A24F 47/008 392/395 |
| 2016/0183596 | A1* | 6/2016 | Rado | A24F 47/008 392/395 |
| 2016/0366945 | A1* | 12/2016 | Rado | A24F 47/008 |
| 2017/0231282 | A1* | 8/2017 | Bowen | A24F 47/008 131/329 |
| 2017/0273359 | A1* | 9/2017 | Liu | A24F 47/008 |
| 2017/0311384 | A1* | 10/2017 | Wu | A61M 11/042 |

* cited by examiner

*Primary Examiner* — Thor Campbell

(57) ABSTRACT

The present invention discloses an atomized liquid storage device, including a container used for storing atomized liquid, where the container is axially provided with a penetrating through hole, an inner wall of the through hole is provided with a liquid outlet hole communicating with an inner part of the container, the through hole is further internally provided with a sealing structure slidable up and down, and the sealing structure seals the liquid outlet hole and is set to allow air in the through hole to pass through. An atomizer is further disclosed, including the atomized liquid storage device and an atomization device. The atomized liquid storage device of the present invention has advantages of a simple structure and good sealing performance, and the atomizer of the present invention has advantages of being convenient and efficient in use and replacement of an atomized liquid storage device.

12 Claims, 6 Drawing Sheets

ATOMIZED LIQUID STORAGE DEVICE AND ATOMIZER

CROSS-REFERENCE TO RELATED APPLICATIONS

The present application claims the benefit of Chinese Patent Application No. 201510609443.5 filed on Sep. 23, 2015; the contents of which are hereby incorporated by reference.

BACKGROUND

Technical Field

The present invention relates to atomization devices, and in particular, to an atomized liquid storage device with a simple structure and good sealing performance and an atomizer that is convenient and efficient in use and replacement of an atomized liquid storage device.

Related Art

An atomizer is mainly used for inhaling fragrance or drugs. There are mainly two manners of replenishing an existing atomizer with atomized liquid during use, one is repeatedly injecting atomized liquid into a liquid receiver, and the other is filling atomized liquid by piercing a liquid slug. The first manner is inconvenient and easily causes contamination, and the second manner easily leads to a situation in which the liquid slug ruptures due to other external factors.

SUMMARY

To resolve the foregoing problem, one objective of the present invention is to provide an atomized liquid storage device with a simple structure and good sealing performance, and another objective of the present invention is to provide an atomizer that is convenient and efficient in use and replacement of an atomized liquid storage device.

The present invention is implemented by means of the following technical measure: An atomized liquid storage device includes: a container used for storing atomized liquid, where the container is axially provided with a penetrating through hole, an inner wall of the through hole is provided with a liquid outlet hole communicating with an inner part of the container, the through hole is further internally provided with a sealing structure that slidable up and down, and the sealing structure seals the liquid outlet hole and is set to allow air in the through hole to pass through.

As one preferred example, an undersurface of the container is provided with an identification code structure.

As one preferred example, the sealing structure is in a shape of a tube abutting against the inner wall of the through hole.

As one preferred example, the through hole is further internally provided with a spring, two ends of the spring respectively abut against the inner wall of the through hole and an upper end of the sealing structure, and the sealing structure compresses the spring when sliding upwards.

The present invention further discloses an atomizer, including: the atomized liquid storage device and an atomization device, where the atomization device is provided thereon with an atomizing tube, the atomizing tube is internally provided with an atomization structure, and the atomizing tube is inserted into the through hole of the atomized liquid storage device in a matching manner, so as to push the sealing structure to slide to make the atomizing tube abut against the inner wall of the through hole and cover the liquid outlet hole.

As one preferred example, the inner wall of the through hole is provided with a guide structure, and an outer wall of the atomizing tube is provided with a positioning structure fitting in with the guide structure of the inner wall of the through hole.

As one preferred example, the atomization structure is a heating atomization structure, a compressing atomization structure or an ultrasonic atomization structure.

As one preferred example, the atomization structure is a heating atomization structure, a tube wall of the atomizing tube is set to be an adsorption layer, an inner wall of the atomizing cup is provided with an electric heating device abutting against the adsorption layer, and the atomizing tube is inserted into the through hole of the atomized liquid storage device in a matching manner, so as to push the sealing structure to slide to make the atomizing tube abut against the inner wall of the through hole and cover the liquid outlet hole.

As one preferred example, an undersurface of the container is provided with an identification code structure, and the atomization device is provided with a code reading structure corresponding to the identification code structure.

As one preferred example, the inner wall of the through hole is provided with a guide structure, and an outer wall of the heating atomizing tube is provided with a positioning structure fitting in with the guide structure of the inner wall of the through hole.

As one preferred example, the inner wall of the through hole is provided with an identification code structure, and the heating atomizing tube is provided with a code reading structure corresponding to the identification code structure.

As one preferred example, the heating atomizing tube is externally provided with a protective shell, and the protective shell is provided thereon with a liquid guiding hole communicating with the liquid outlet hole.

As the inner wall of the atomized liquid storage device of the present invention is provided with the liquid outlet hole, and the through hole is further internally provided with the sealing structure that can slide up and down, when the atomized liquid storage device is not in use, the sealing structure covers and seals the liquid outlet hole, and when the atomized liquid storage device is to be used, the atomizing tube on the atomization device is inserted into the through hole, and the atomizing tube makes the sealing structure slide upwards, so that the atomizing tube covers the liquid outlet hole, the atomized liquid in the container permeates from the liquid outlet hole into the atomizing tube, the atomization structure disposed in the atomizing tube operates to atomize the atomized liquid, and air flowing through the through hole is inhaled together with atomized vapor into the human body. The atomized liquid storage device of the present invention has advantages of a simple structure and good sealing performance, and the atomizer of the present invention has advantages of being convenient and efficient in use and replacement of an atomized liquid storage device.

BRIEF DESCRIPTION OF THE DRAWINGS

FIG. 1 is a schematic structural diagram of an atomized liquid storage device according to an embodiment of the present invention;

FIG. 2 is a sectional view of an atomized liquid storage device according to an embodiment of the present invention;

FIG. 3 is a schematic structural diagram of an atomized liquid storage device according to another embodiment of the present invention;

DETAILED DESCRIPTION

Figure 1:
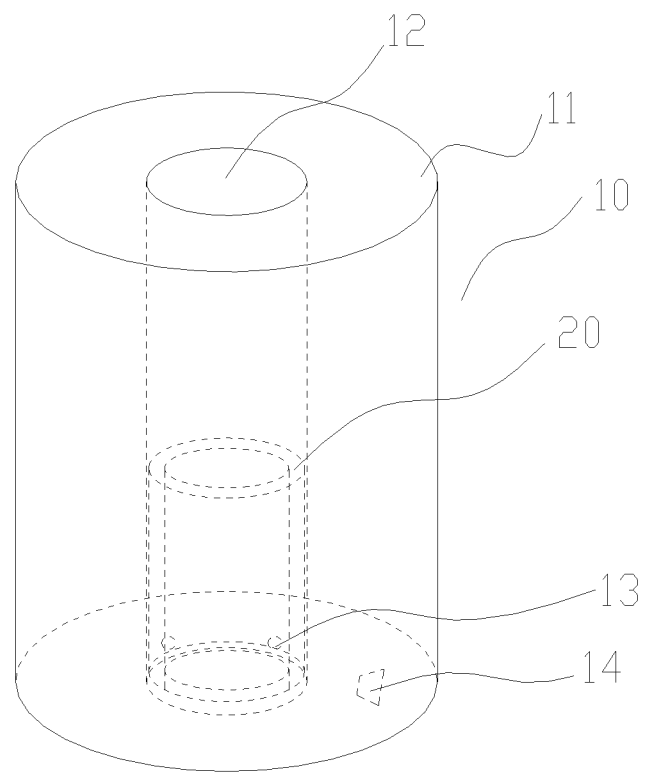
Figure 2:
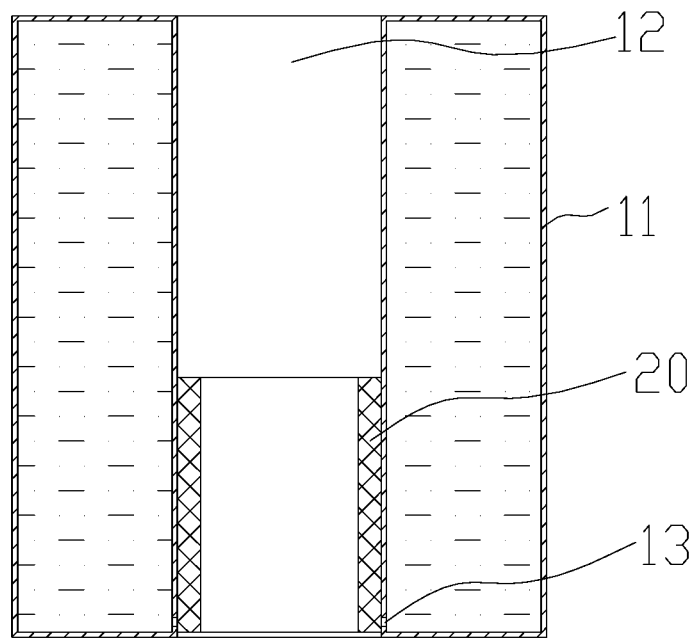
Figure 3:
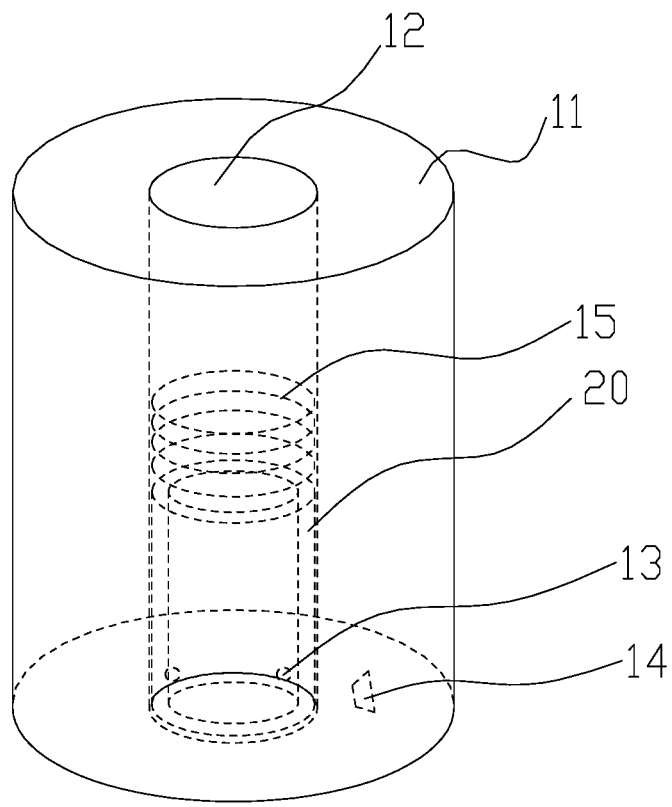
Figure 4:
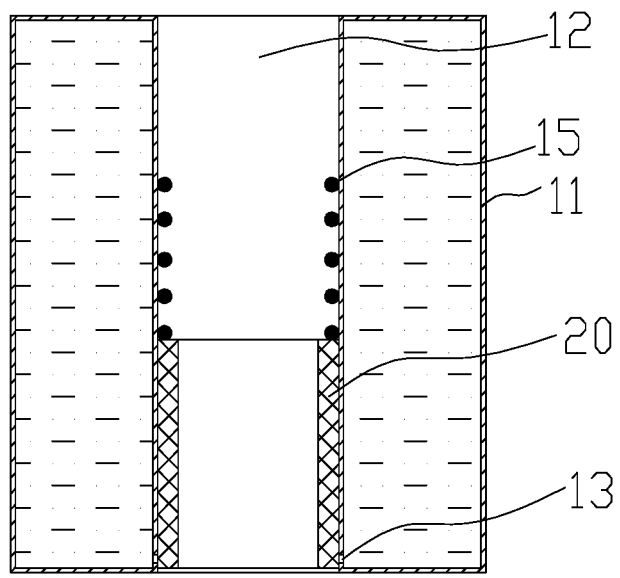
FIG. 4 is a sectional view of an atomized liquid storage device according to another embodiment of the present invention.
Figure 5:
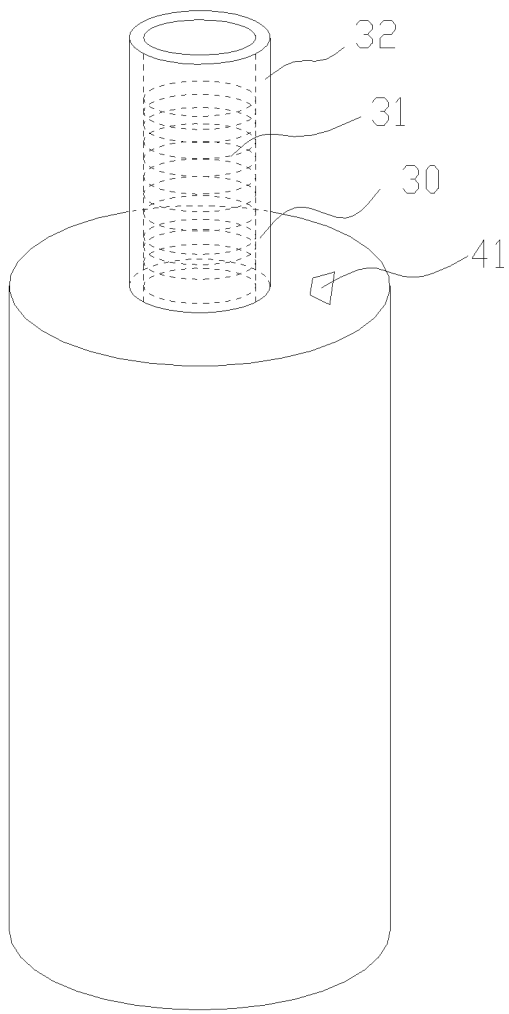
FIG. 5 is a schematic structural diagram of an atomization device according to an embodiment of the present invention.
Figure 6:
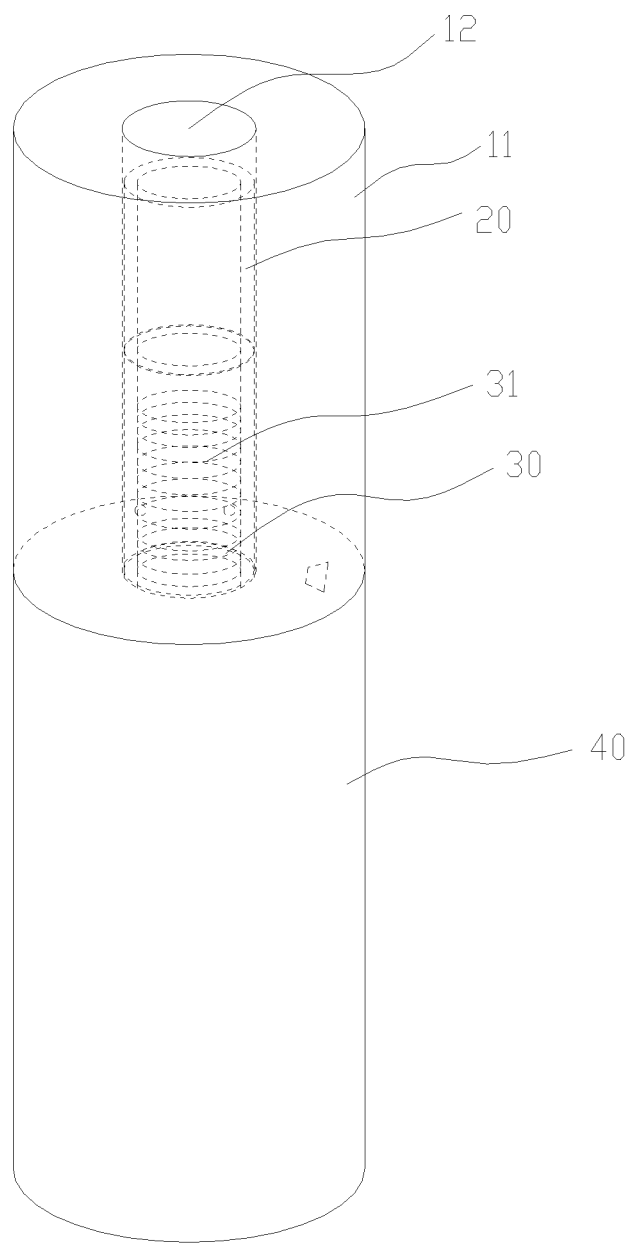
FIG. 6 is a schematic structural diagram of an atomizer according to an embodiment of the present invention.
Figure 7:
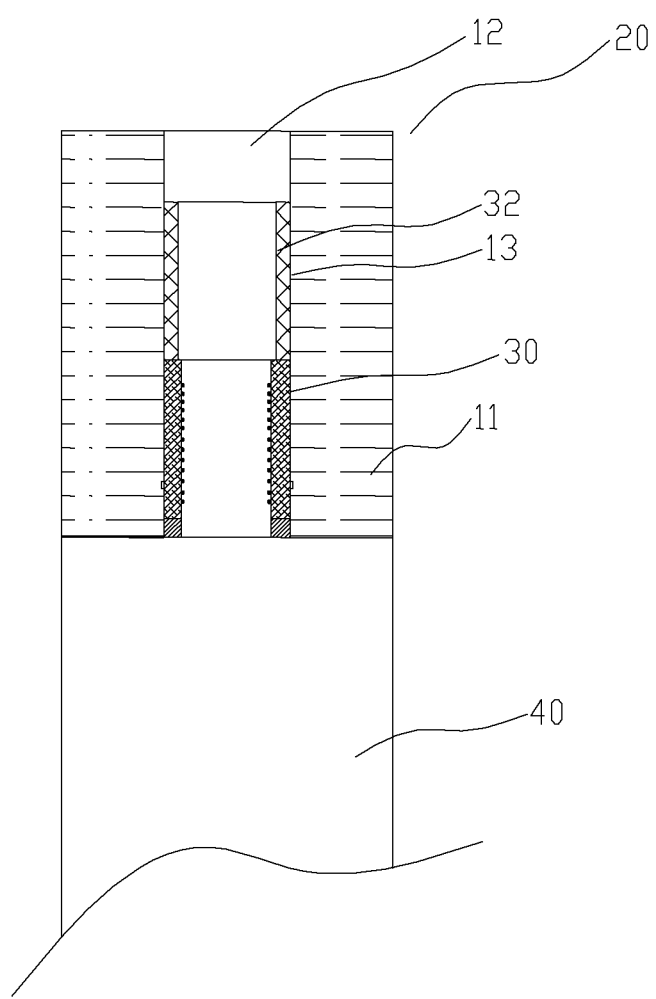
FIG. 7 is a sectional view of an atomizer according to an embodiment of the present invention.
Figure 8:
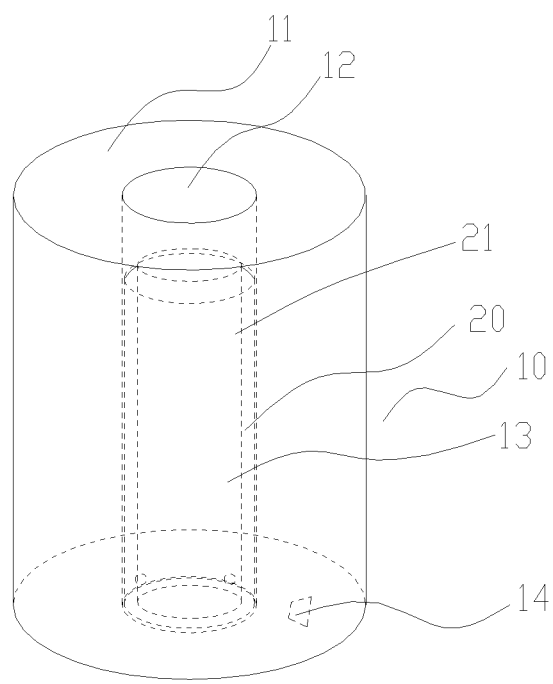
FIG. 8 is a schematic structural diagram of an atomized liquid storage device according to another embodiment of the present invention.
Figure 9:
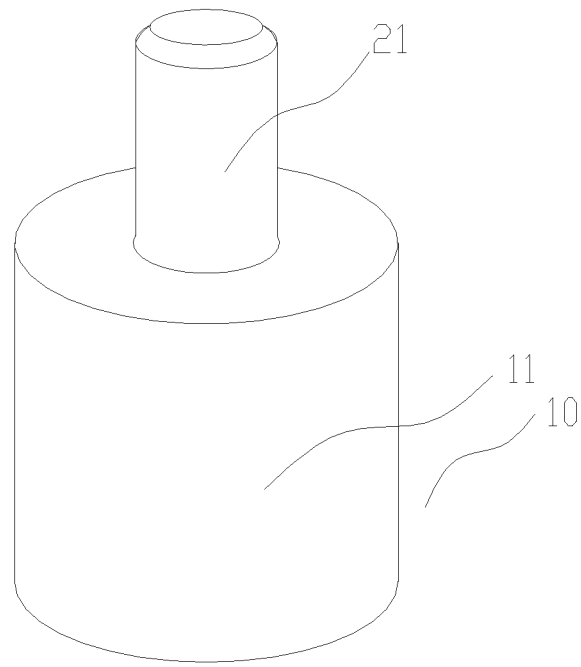
FIG. 9 is a schematic structural diagram of operation of an atomized liquid storage device according to another embodiment of the present invention.

An atomizer of this embodiment, referring to FIG. 1 to FIG. 9, includes an atomized liquid storage device 10 and an atomization device 40, where the atomized liquid storage device 10 includes a container 11 used for storing atomized liquid, the container 11 is axially provided with a penetrating through hole 12, a liquid outlet hole 13 communicating with an inner part of the container is disposed on a lower part of an inner wall of the through hole 12, the liquid outlet hole 13 may be formed by multiple small holes, or may be a strip-type hole, the through hole 12 is further internally provided with a sealing tube 20 that can slide up and down, and the sealing tube 20 seals the liquid outlet hole 13 and is set to allow air in the through hole 12 to pass through. The atomization device 40 is provided thereon with a heating atomizing tube 30, the heating atomizing tube 30 is provided with an adsorption layer 32, an inner wall of the heating atomizing tube 30 is provided with an electric heating device 31 (a heating wire, an electric heating piece, or the like) abutting against the adsorption layer 32, and the heating atomizing tube 30 is inserted into the through hole 12 of the atomized liquid storage device in a matching manner, so as to push the sealing tube 20 to slide upwards to make the heating atomizing tube 30 abut against the inner wall of the through hole 12 and cover the liquid outlet hole 13. Certainly, in other embodiments, the atomization structure in the atomization device may also be a compressing atomization structure or an ultrasonic atomization structure.

As the inner wall of the atomized liquid storage device 10 of the atomizer is provided with the liquid outlet hole 13 and the through hole 12 is further internally provided with the sealing tube 20 that can slide up and down, when the atomized liquid storage device 10 is not in use, the sealing tube 20 covers and seals the liquid outlet hole 13, and when the atomized liquid storage device 10 is to be used, the heating atomizing tube 30 on the atomization device 40 is inserted into the through hole 12, and the heating atomizing tube 30 makes the sealing tube 20 slide upwards, so that the heating atomizing tube 30 covers the liquid outlet hole 13, the atomized liquid in the container permeates from the liquid outlet hole 13 into the adsorption layer 32, the electric heating device 31 (the heating wire, the electric heating piece, or the like) disposed on the adsorption layer 32 operates to heat and atomize the atomized liquid on the adsorption layer 32, and air flowing through the through hole 12 is inhaled together with atomized vapor into the human body. The atomized liquid storage device has a simple structure, and has good sealing performance as the sealing tube 20 is disposed in the through hole and is not easy to disconnect by external factors, and the atomizer is convenient and efficient in use and replacement of an atomized liquid storage device. The atomizer can be used in electronic cigarettes, drug atomization treatment, and the like.

An atomizer of this embodiment, referring to FIG. 1, FIG. 3, FIG. 5 and FIG. 7, on the basis of the foregoing technical solution, may specifically be as follows: an undersurface of the container 11 is provided with an identification code structure 14, and the atomization device 40 is provided with a code reading structure 41 corresponding to the identification code structure 14. For example, the undersurface of the container 11 is provided with conductive contacts with a certain arrangement, the atomization device 40 is provided with a conductive contact array corresponding to the conductive contacts, and when the atomization device 40 is inserted into the atomized liquid storage device 10 in a matching manner, the atomization device 40 can operate only when correct contacts in the conductive contact array of the atomization device 40 are switched on, and otherwise, the atomization device 40 cannot be powered for operation, so as to ensure matching use of the atomization device 40 and the atomized liquid storage device 10. Similarly, it is also feasible to dispose a radio frequency tag, a two-dimensional code, an NFC tag or the like on the undersurface of the container 11, and dispose a corresponding reading module at a corresponding position of the atomization device 40, which can also ensure matching use of the atomization device and the atomized liquid storage device.

An atomization device 40 of another embodiment, referring to FIG. 3 and FIG. 4, on the basis of the foregoing technical solution, may specifically be as follows: the through hole 12 is further internally provided with a spring 15, two ends of the spring 15 respectively abut against the inner wall of the through hole 12 and an upper end of the sealing tube 20, when the heating atomizing tube 30 is inserted into the through hole 12 of the atomized liquid storage device in a matching manner, the sealing tube 20 is pushed to slide upwards and compress the spring 15, and when the heating atomizing tube 30 is pulled out, a restoration of the spring 15 pushes the sealing tube 20 to slide downwards to seal the liquid outlet hole 13, thereby facilitating detachment of the atomized liquid storage device 10 and the atomization device 40 when not in use.

An atomizer of another embodiment, referring to FIG. 8 and FIG. 9, on the basis of the foregoing technical solution, may specifically be as follows: an upper part 21 of the sealing tube 20 is set to be in the shape of a suction nozzle, and when the sealing tube 20 slides upwards, the upper part in the shape of the suction nozzle 21 slides out of the through hole 12 to form a suction nozzle, so as to avoid that the part touched by the human mouth is contaminated.

An atomizer of this embodiment, on the basis of the foregoing technical solution, may specifically be as follows: the inside of the sealing tube is provided with a filter tip structure, so as to use the filter tip structure to filter small particles and droplets in atomized vapor. An atomizer of this embodiment, on the basis of the foregoing technical solution, may specifically be as follows: the through hole is set to be non-circular, so as to ensure that, after the heating atomizing tube slides in the through hole, the adsorption layer (when disposed on only some parts of the heating atomizing tube) of the heating atomizing tube can correctly cover the liquid outlet hole.

An atomizer of this embodiment, on the basis of the foregoing technical solution, may specifically be as follows:

the inner wall of the through hole is provided with a guide structure, and an outer wall of the heating atomizing tube is provided with a positioning structure fitting in with the guide structure of the inner wall of the through hole. For example, the inner wall of the through hole is axially provided with a guide slot, an outer wall of the heating atomizing tube is provided with a raised positioning column, and the positioning column slides in the guide slot, so as to ensure that, after the heating atomizing tube slides in the through hole, the adsorption layer (when disposed on only some parts of the heating atomizing tube) of the heating atomizing tube can correctly cover the liquid outlet hole. An atomizer of this embodiment, on the basis of the foregoing technical solution, may specifically be as follows: it is also feasible to dispose a metallic protective shell outside the adsorption layer, and dispose, on the protective shell, a liquid guiding hole communicating with the liquid outlet hole, so as to protect the adsorption layer therein by using the metallic protective shell.

An atomizer of this embodiment, on the basis of the foregoing technical solution, may specifically be as follows: the through hole is a truncated conical through hole which gradually becomes bigger from top to bottom, so as to ensure that the adsorption layer can closely cover the liquid outlet hole, and certainly, upper and lower radiuses are differed a little.

The above describes the heating atomization device of the present invention and is used to help understand the present invention, but embodiments of the present invention are not limited to the foregoing embodiments, and any change, modification, replacement, combination and simplification made without departing from the principle of the present invention should be equivalent substitution manners and should be encompassed in the protection scope of the present invention.

What is claimed is:

1. An atomized liquid storage device, comprising: a container used for storing atomized liquid, wherein the container is axially provided with a penetrating through hole, an inner wall of the through hole is provided with a liquid outlet hole communicating with an inner part of the container, the through hole is further internally provided with a sealing structure slidable up and down, and the sealing structure seals the liquid outlet hole and is set to allow air in the through hole to pass through;
wherein the through hole is further internally provided with a spring, two ends of the spring respectively abut against the inner wall of the through hole and an upper end of the sealing structure, and the sealing structure compresses the spring when sliding upwards.

2. The atomized liquid storage device according to claim 1, wherein an undersurface of the container is provided with an identification code structure.

3. The atomized liquid storage device according to claim 1, wherein the sealing structure is in a shape of a tube abutting against the inner wall of the through hole.

4. The atomized liquid storage device according to claim 2, wherein the sealing structure is in a shape of a tube abutting against the inner wall of the through hole.

5. An atomizer, comprising: the atomized liquid storage device according to claim 1 and an atomization device, wherein the atomization device is provided thereon with an atomizing tube, the atomizing tube is internally provided with an atomization structure, and the atomizing tube is inserted into the through hole of the atomized liquid storage device in a matching manner, so as to push the sealing structure to slide to make the atomizing tube abut against the inner wall of the through hole and cover the liquid outlet hole.

6. The atomizer according to claim 5, wherein the inner wall of the through hole is provided with a guide structure, and an outer wall of the atomizer is provided with a positioning structure fitting in with the guide structure of the inner wall of the through hole.

7. The atomizer according to claim 5, wherein the atomization structure is a heating atomization structure, a compressing atomization structure or an ultrasonic atomization structure.

8. The atomizer according to claim 7, wherein the atomization structure is the heating atomization structure, a tube wall of the atomizing tube is set to be an adsorption layer, an inner wall of the atomizing tube is provided with an electric heating device abutting against the adsorption layer, and the atomizing tube is inserted into the through hole of the atomized liquid storage device in a matching manner, so as to push the sealing structure to slide to make the atomizing tube abut against the inner wall of the through hole and cover the liquid outlet hole.

9. The atomizer according to claim 5, wherein an undersurface of the container is provided with an identification code structure, and the atomization device is provided with a code reading structure corresponding to the identification code structure.

10. The atomizer according to claim 5, wherein the atomizing tube is a heating atomizing tube, the heating atomizing tube is externally provided with a protective shell, and the protective shell is provided thereon with a liquid guiding hole communicating with the liquid outlet hole.

11. The atomizer according to claim 5, wherein the sealing structure is in a shape of a tube abutting against the inner wall of the through hole.

12. The atomizer according to claim 5, wherein the through hole is further internally provided with a spring, two ends of the spring respectively abut against the inner wall of the through hole and an upper end of the sealing structure, and the sealing structure compresses the spring when sliding upwards.

* * * * *